(12) United States Patent
Amir et al.

(10) Patent No.: US 6,206,891 B1
(45) Date of Patent: Mar. 27, 2001

(54) DEVICE AND METHOD FOR CALIBRATION OF A STEREOTACTIC LOCALIZATION SYSTEM

(75) Inventors: Avner Amir, Ramat Yishay; Alexander Studnitzki, Kiriat Bialik, both of (IL)

(73) Assignee: MedEye Medical Technology Ltd., Migdal Haemek (IL)

( * ) Notice: Subject to any disclaimer, the term of this patent is extended or adjusted under 35 U.S.C. 154(b) by 0 days.

(21) Appl. No.: 09/395,569

(22) Filed: Sep. 14, 1999

(51) Int. Cl.[7] .................................................. A61B 19/00

(52) U.S. Cl. .............................................................. 606/130

(58) Field of Search .................................... 606/130, 129; 378/901, 205, 206, 207; 600/429, 417

(56) References Cited

U.S. PATENT DOCUMENTS

| | | | |
|---|---|---|---|
| 4,791,934 | * 12/1988 | Brunnett | 606/130 |
| 5,354,314 | * 10/1994 | Hardy et al. | 606/130 |
| 5,603,318 | * 2/1997 | Heilbrun et al. | 606/130 |
| 6,009,189 | * 12/1999 | Schaack | 382/154 |
| 6,052,611 | * 4/2000 | Yanof et al. | 606/130 |
| 6,069,932 | * 5/2000 | Peshkin et al. | 606/130 |
| 6,081,336 | * 6/2000 | Messner et al. | 606/130 |

* cited by examiner

Primary Examiner—Pedro Philogene
(74) Attorney, Agent, or Firm—Venable; Robert Kinberg

(57) ABSTRACT

A device for use in obtaining one or more calibration parameters of an array of two-dimensional sensors used in stereotactic localization of objects in a workspace. The device comprises a target array and a positioner capable of positioning the target array at a desired location in the workspace.

26 Claims, 2 Drawing Sheets

DEVICE AND METHOD FOR CALIBRATION OF A STEREOTACTIC LOCALIZATION SYSTEM

FIELD OF THE INVENTION

The present invention relates to devices for stereotactic localization of an object in space, especially, but not limited to, such devices for use in localizing an instrument during a medical procedure.

BACKGROUND OF THE INVENTION

Stereotactic localization refers to the localization of an object in a three-dimensional workspace by means of two or more two-dimensional sensors viewing the object along different sight lines. A three-dimensional coordinate system is established in the workspace and the three-dimensional coordinates of the object are calculated from the two-dimensional views obtained by the sensors. Stereotactic localization is important, for example, during invasive surgery when it is necessary to locate in the operating space, with a high degree of accuracy, part of a surgical instrument. For example, the location of the exposed handle of a probe in the operating space may be determined, from which the location of the tip of the probe inside the patient's body may be calculated. In such cases, the location of the tip may be registered in a displayed computerized image of the patient, such as an X-ray, sonogram, or CAT scan.

The sensors used in stereotactic localization may be cameras that sense light emitted by objects to be detected in the workspace. Devices utilizing video cameras as sensors are described in L. Adams, et al., IEEE Computer Graphics and Application Vol. 10 (1990), No. 3, pp. 43–51; M. P. Helibrun, et al., Stereotactic and Functional Neurosurgery 1992, No. 58, pp. 94–98; N. Meitland et al., Proceedings of the $5^{th}$ British Machine Vision Conference, York, BMVA Press, 1994 pp. 609–618 and in U.S. Pat. Nos. 5,603,318 and 5,792,147. Alternatively, the objects of interest may be modified to emit another form of energy detected by the sensors. The type of energy used may be radio-frequency radiation (as disclosed in U.S. Pat. No. 5,251,635), sound waves (U.S. Pat. No. 4,012,588), or pulsed DC magnetic fields (U.S. Pat. No. 5,558,091). Devices based on the detection of pulsed infrared light radiation by video cameras are disclosed in U.S. Pat. Nos. 5,622,170, 5,197,476 and 5,792,147.

An array of two-dimensional sensors to be used in stereotactic localizing systems must be calibrated prior to use in order to establish the relative orientation of the sensors in the array and other parameters necessary for locating objects in space. In one calibration procedure, a plurality of target objects are placed in the workspace at points of known three-dimensional coordinates, and stereotactic views of the targets are obtained by the sensors. The resulting calibration data are then used to generate a localization function determining the three-dimensional coordinates of an object in the workspace from the two-dimensional stereotactic views of it obtained by the sensors. Computation of a localization function is described, for example, in Jain, R. et al., *Machine Vision*, McGraw-Hill, New York 1995. The localization function involves 14 parameters that are calculated from the calibration data. Six of these parameters characterize sensor positions and orientation, two characterize the sensor projections of the focal plane, four characterize optical distortion of the lens, and two characterize scaling factors and aspect ratio. The accuracy of the calculated camera parameters, and hence of the localization function, is limited by the number of target points used for obtaining the calibration data. For the localization function to be accurate in the entire workspace, calibration data must be obtained over a set of target points spanning as large a volume in the workspace as possible and being as dense as possible in that volume.

U.S. Pat. No. 5,603,318 discloses a device consisting of a small number of targets attached to the patient that serve for calibration of sensors in a medical stereotactic procedure. Since the number of targets used for the calibration is small, and is necessarily located outside the patient's body, the calibration data yielded are accurate only near the targets. The accuracy rapidly diminishes to intolerable levels at locations away from the targets including locations of medical interest (e.g. inside a patient's body). This calibration method necessitates that it be performed in the workspace and that the calibration device be present in the workspace during the medical procedure.

Alternative methods in the art use a fixed planar or box-type three-dimensional calibrating target that provides at least three surfaces as calibrating targets. These devices also do not have a sufficiently high target density to provide accurate calibration data for high accuracy localization during a medical procedure.

SUMMARY OF THE INVENTION

The present invention provides a device and method for obtaining calibration data in a fixed coordinate system for calibrating an array of two-dimensional sensors to be used in stereotactic localization. The calibration system produces calibration data on a dense array of target points (typically several thousand) spanning the entire workspace and is not physically present in the workspace when subsequent localization determinations are performed. The calibration data yielded by the invention allow accurate calculation of the sensor array parameters and this, in turn, allows localization of objects in the workspace with a high degree of accuracy.

The invention permits subsequent localization of objects without the calibration device being present in the workspace and without having to carry out the calibration process in the same workspace as the localization is to take place.

In accordance with the invention an array of one or more targets is mounted on a positioner that sequentially positions the target array at a large number of locations in the workspace. At each location, accurate positional information of the center of each target in the array is obtained. At each location, two-dimensional sensor views of the target are also obtained.

The invention may further comprise means for calibrating the sensors, or means for calculating a localization function, from the calibration data. Since all sensors are calibrated simultaneously and a large number (several thousand) of target points are used in calibration, accurate values of the camera parameters are obtained. The invention may be used in localizing part of a surgical instrument during a medical procedure. In this case, the invention may comprise means for registering a localized part in a displayed computerized image of the patient such as an x-ray image, magnetic resonant image, or a computerized tomographic image.

The invention thus provides a device for use in obtaining one or more calibration parameters of an array of two-dimensional sensors used in stereotactic localization of objects in a workspace, the device comprising:

(a) a target array comprising one or more targets; and
(b) a positioner capable of positioning the target array at a desired location in the workspace.

The invention further provides a method for obtaining one or more calibration parameters of an array of two-dimensional sensors used in stereotactic localization of objects in a workspace, each sensor in the sensor array viewing the workspace along a fixed sight line and producing a signal characteristic of its view of the workspace, the method comprising:

(a) positioning a target array at one or more desired locations in the workspace;

(b) for each of the one or more desired locations, processing the signals produced by one or more sensors in the sensor array; and (c) calculating the one or more calibration parameters of the sensor array.

BRIEF DESCRIPTION OF THE DRAWINGS

In order to understand the invention and to see how it may be carried out in practice, a preferred embodiment will now be described, by way of non-limiting example only, with reference to the accompanying drawings, in which.

DETAILED DESCRIPTION OF A PREFERRED EMBODIMENT

Figure 1:
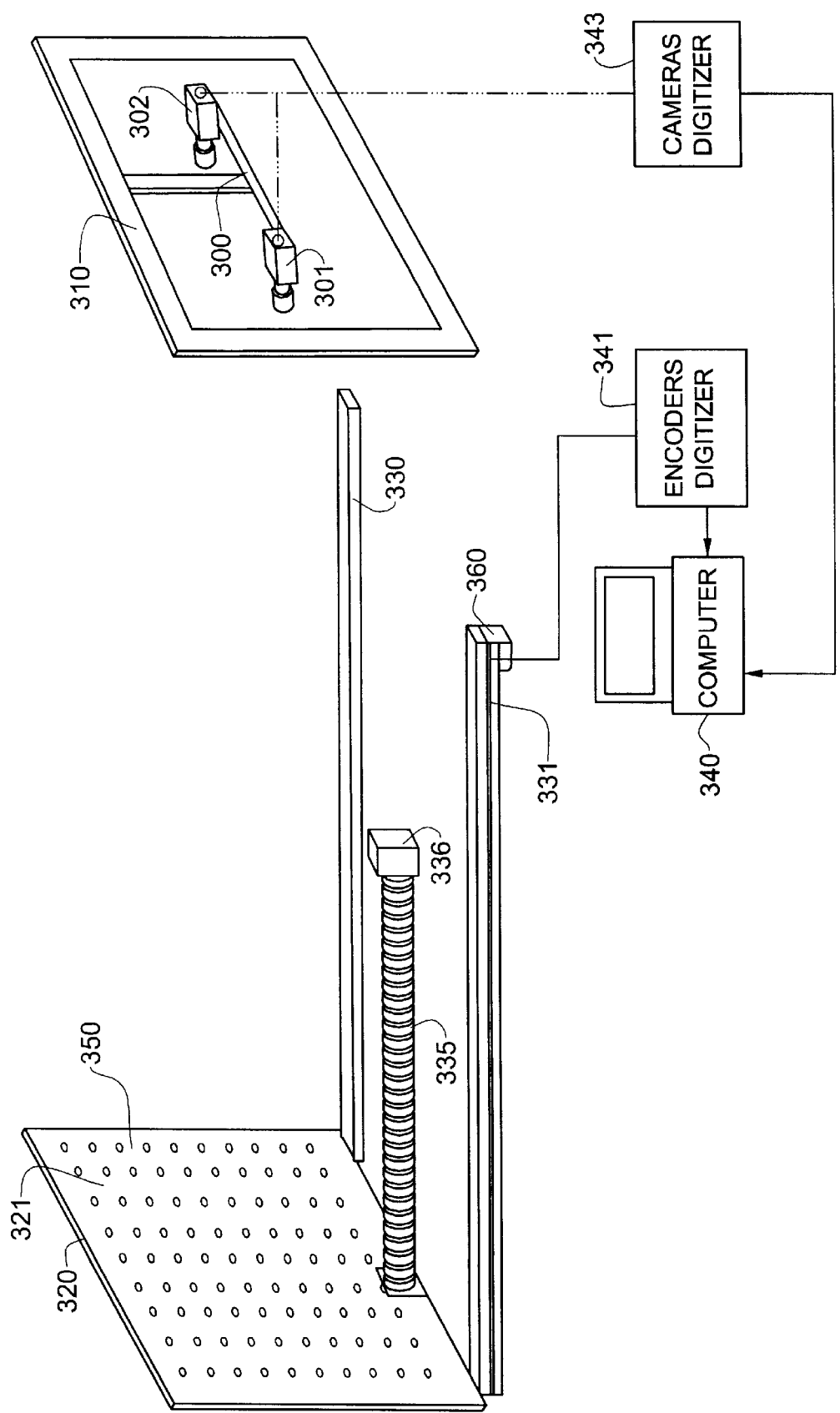
FIG. 1 shows a calibration device according to one embodiment of the invention.

Referring first to FIG. 1, sensors 301 and 302 are mounted on a bracket 300 that fixes the sight line along where each sensor views the workspace. Bracket 300 is attached to a stationary holder 310. A planar target holder 320 displaying target pattern 321 is placed in the workspace. The target pattern 321 consists of a two-dimensional array of targets 350, for example, a 30×30 grid of small circles produced by a high accuracy printing process over the planar target holder 320. The target holder 320 is translatable along an axis perpendicular to its surface by along tracks 330 and 331 and may be positioned at any position along the tracks 330 and 331. A typical translation mechanism is a bolt 335 at the center bottom of the target holder that is made to pull or push the plate as it turns. The bolt may be turned manually or by a controlled motor. As the target holder 320 is translated along the tracks 330 and 331, it is made to stop at any desired location along the tracks 330 and 331. The position of the target holder 320 along the tracks 330 and 331 is registered by a linear encoder 360 such as a Heidenhain LS Series Encoder having 5 µm resolution. The encoder 360 provides positional information of the target holder 320 along the tracks 330 and 331 in the form of an electrical signal that is input to an encoder digitizer 341. The digitized image data are input to a computer processing unit 340 which may be, for example, a suitably programmed personal computer.

Sensors 301 and 302 form a sensor array to be calibrated. While only two sensors are depicted, the device and method of the invention may be used with sensor arrays comprising any number of sensors. At each location at which the target holder 320 has been stopped, the sensors 301 and 302 record an image of the target pattern 321. The target holder 320 may additionally be mounted on a two-dimensional translator, which provides for transverse motion of the target holder 320 in its plane at each point along the tracks 330 and 331 where it has been positioned. This provides an even higher density of target locations in its plane resulting in higher accuracy of the obtained calibration parameters.

The image data are input to a camera digitizer 343 and the digitized image data are input to the computer processing unit 340. The series of frames grabbed by each camera at the sequential positions along the tracks 330 and 331 thus produce a three-dimensional array of target positions. For cameras having a 12.5 mm focal length lens and a standard 768×576 CCD sensor, a relative error of less than 1 in 30,000 in the image plane can be obtained.

Computer processing unit 340 carries out a mathematical computation on the images that detects each target 350 in each of the images. The two-dimensional coordinates of the center of each target in each camera view are obtained by a known image processing method such as described in Jain, R. Kasturi and B. G. Schunk: *Machine Vision*, (McGraw-Hill, New York 1995).

Figure 2:
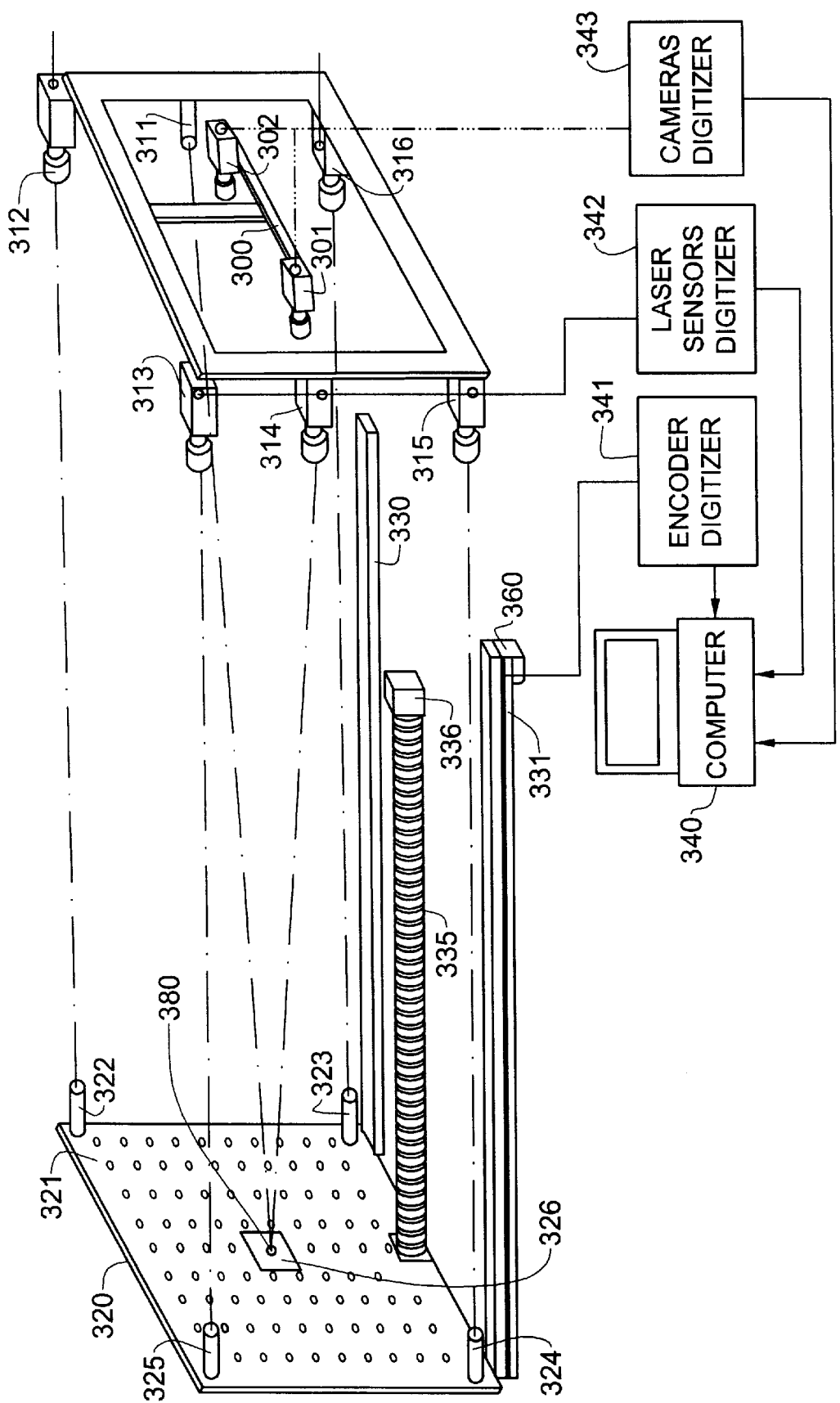
FIG. 2 shows another embodiment of the invention comprising means for measuring rotation and transverse displacement of the target holder.

FIG. 2 shows another embodiment of the invention, in which components identical to those shown in FIG. 1 are indicated by the same numerals. The embodiment shown in FIG. 2 comprises means for correcting the calculated target locations for any inadvertent rotational movement or transverse displacement of the target holder 320 that may occur as it is translated along the tracks 330 and 331. At each step of the motion of the target holder 320, a sensor 314, for example, a CCD camera filtered for laser light, acquires images of a laser spot 380 produced by a laser 311 on a reflecting surface 326. The images obtained by the sensor 314 are digitized by a digitizer 342 and input to a computer processing unit 340. The beams from lasers 322, 323, 324, and 325 are detected by laser sensors 312, 313, 315, and 316 respectively. The location of the center of each of the four detected spots in three-dimensional space is described by a three-dimensional vector $r_i$, for i=0, 1, 2, 3. The following set of vector equations holds:

$$dr_{i0} = \theta_R \times \rho_{i0} + (\theta_P + \theta_Y) \times z_{i0}, \; i=1,2,3, \quad (1)$$

wherein × denotes vector cross product, $r_{i0}=r_i-r_0$ (i=1, 2, 3), $\rho_{i0}$ and $z_{i0}$ are the transverse and axial components, respectively, of the motion of the target holder 320, and $\theta_R$, $\theta_P$ and $\theta_Y$ are respectively the roll, pitch and yaw angles of the target holder 320 relative to the camera holder 310. $dr \neq 0$ is indicative of rotational movement of the target holder 320. Equation (1) may be solved for $\theta_R$, and $\theta_P + \theta_Y$ by methods known in the art, for example, as described in Press et al., Numerical Recipes in C, the Art of Scientific computing. Cambridge Press, 1992. Alternatively, $\theta_P$ and $\theta_Y$ first be calculated by the computer processing unit 340 from the location of the image of the laser spot 380 in the field of view of the laser sensor 314, and then (1) is solved for $\theta_R$ alone. The obtained values of $\theta_R$, $\theta_P$ and $\theta_Y$ are then used to correct the calculated locations of the targets.

Once the calibration data have been obtained, the calibration parameters of the camera system are obtained as is known in the art for example, as described in Jain, R. et al., *Machine Vision,* McGraw-Hill, New York 1995. Once the camera parameters have been determined, a localizing function may be derived as is known in the art, for example as disclosed in Jain, R. et al., *Machine Vision,* McGraw-Hill, New York 1995.

In a medical application of the invention, the invention may further comprise an immobilizer for immobilizing a part of a patient's body in the workspace. The immobilizer may have one or more reference objects rigidly affixed onto it that can be identified by the computer processing unit when in the view of a sensor from the sensor array. The computer processing unit may further be capable of localizing the reference objects in the workspace and registering them in an image of part of the patient's body. The computer processing unit may also be capable of identifying and localizing one or more portions of a medical instrument in the workspace, determining the orientation of the medical instrument in the workspace, and registering the location of a desired portion of the medical instrument in an image of the patient's body.

What is claimed is:

1. A device for use in obtaining one or more calibration parameters of an array of two-dimensional sensors used in stereotactic localization of objects in a workspace, the device comprising:

(a) a two-dimensional array of targets; and
   (b) a positioner capable of positioning the array at a plurality of desired locations in the workspace.

2. The device of claim 1, wherein the target array is a two-dimensional array of shapes printed on a planar surface.

3. The device of claim 1, wherein the target array is positioned at a desired location by being translated along one or more axes until it is positioned at the desired location in the workspace.

4. The device of claim 1, further comprising a computer processing unit having a memory.

5. The device of claim 4, wherein the location of one or more targets in the target array are input to the computer processing unit.

6. The device of claim 4, further comprising an array of two-dimensional sensors, each sensor viewing the workspace along a selectable sight line, each sensor producing an analogue signal characteristic of its view of the workspace.

7. The device according to claim 6, further comprising an analogue to digital converter for digitizing the analogue signal produced by each sensor in the sensor array.

8. The device of claim 7, further comprising a sensor array controller capable of synchronizing image acquisition by the sensors in the sensor array.

9. The device of claim 8, wherein the digital signals of one or more sensors in the sensor array are input to the computer processing unit.

10. The device of claim 8, wherein the location of one or more targets in the target array are input to the computer processing unit, and the digital signals of one or more sensors in the sensor array are input to the computer processing unit.

11. The device of claim 10, wherein the computer processor is capable of identifying targets in the view of one or more of the sensors.

12. The device of claim 11, wherein one or more calibration parameters of the sensor array are calculated by the computer processing unit.

13. The device of claim 12, wherein the target array is translated along one or more axes until it is positioned at a desired location in the workspace and the calculated calibration parameters are corrected for any rotation of the target array about an axis as the target array is translated.

14. The device of claim 12, wherein the computer processing unit is further capable of generating a localization function.

15. The device of claim 14, further comprising an immobilizer for immobilizing part of a patient's body in the workspace.

16. The device of claim 15, further comprising one or more reference objects rigidly fixed to the immobilizer, and wherein the computer processing unit is capable of identifying any reference objects in a sensor view of a sensor in the sensor array.

17. The device of claim 16, wherein the computer processing unit is capable of localizing the reference objects in the workspace.

18. The device of claim 17, wherein the computer processing unit is capable of registering the locations of reference objects in the workspace in an image of part of the patient's body.

19. The device according to claim 14, wherein the computer processing unit is capable of identifying and localizing in the workspace one or more predetermined objects in the workspace.

20. The device according to claim 18, wherein the computer processor is capable of identifying and localizing in the workspace one or more predetermined objects in the workspace.

21. The device according to claim 20, wherein one or more of the predetermined objects are one or more portions of one or more medical instruments.

22. The device according to claim 21, wherein the computer processing unit is further capable of determining the location and orientation of the one or more medical instruments in the workspace, and registering the location of a desired portion of the medical instrument in an image of the patient's body.

23. A method for obtaining one or more calibration parameters of an array of two-dimensional sensors used in stereotactic localization of objects in a workspace, each sensor in the sensor array viewing the workspace along a fixed sight line and producing a signal characteristic of its view of the workspace, the method comprising:

(a) positioning a two-dimensional target array at each of a plurality of desired locations in the workspace;
   (b) for each of the desired locations, processing the signals produced by one or more sensors in the sensor array; and
   (c) calculating the one or more calibration parameters of the sensor array based upon the processed signals obtained on at least two positions.

24. The method of claim 23, wherein the target array is a two-dimensional array of shapes printed on a planar surface.

25. The method of claim 23, wherein the target array is positioned by being translated along one or more axes until it is positioned at any one of the desired locations in the workspace.

26. The method of claim 25, wherein the calculated calibration parameters are corrected for any rotation of the target array about an axis as the target array is translated.

* * * * *